United States Patent
Wallace

Patent Number: 5,981,176
Date of Patent: Nov. 9, 1999

[54] METHOD OF DETECTING AND DISCRIMINATING BETWEEN NUCLEIC ACID SEQUENCES

[75] Inventor: R. Bruce Wallace, Greenbrae, Calif.

[73] Assignee: City of Hope, Duarte, Calif.

[21] Appl. No.: 08/193,039

[22] PCT Filed: Jun. 17, 1992

[86] PCT No.: PCT/US92/05133

§ 371 Date: Feb. 4, 1994

§ 102(e) Date: Feb. 4, 1994

[87] PCT Pub. No.: WO93/25563

PCT Pub. Date: Dec. 23, 1993

[51] Int. Cl.$^6$ .............. C12Q 1/68; C12P 19/34; C07H 21/04; C07H 21/02

[52] U.S. Cl. .......... 435/6; 435/91.2; 536/24.33; 935/77; 935/78

[58] Field of Search ............ 435/6, 91.2; 536/24.33; 935/77, 78

[56] References Cited

U.S. PATENT DOCUMENTS

| | | | |
|---|---|---|---|
| 4,656,127 | 4/1987 | Mundy | 435/6 |
| 4,683,195 | 7/1987 | Mullis et al. | 435/6 |
| 4,851,331 | 7/1989 | Vary et al. | 435/6 |
| 5,137,806 | 8/1992 | LeMaistre et al. | 435/6 |

FOREIGN PATENT DOCUMENTS

| | | |
|---|---|---|
| 416817 | 3/1991 | European Pat. Off. . |
| 8910414 | 11/1989 | WIPO . |
| 9009455 | 8/1990 | WIPO . |
| 9011372 | 10/1990 | WIPO . |
| 9113075 | 9/1991 | WIPO . |

OTHER PUBLICATIONS

Maniatis et al., Molecular Cloning, A Laboratory Manual, pp. 388–389, Cold Spring Harbor Laboratory, New York, 1982.
copy of search report for EP 92914420.2–2110 (PCT/US92/05133).
Wu et al., PNAS (USA) 86: 2757–2760 (Apr. 1989).
Syränen et al., Genomics 8:684–692 (1990).

*Primary Examiner*—Stephanie S. Zitomer
*Attorney, Agent, or Firm*—Rothwell, Figg, Ernst & Kurz, p.c.

[57] ABSTRACT

The present invention is directed to a method for detecting the presence or absence of any specific target nucleic acid sequence contained in a sample. The target sequence can be present in the sample in a relatively pure form or as a component of a member of a mixture of different nucleic acids. The method of the invention utilizes a novel primer design. The sequence of the novel primer is composed of two portions, the 3' portion is a primer specific for the desired nucleic acid sequence and the 5' portion is complementary to preselected nucleic acid sequence. Extension of the 3' portion of the primer with a labeled deoxynucleosides triphosphate yields a labeled extension product if, but only if, the template includes the target sequence. The labeled extension product is detected by hybridization of the 5' portion to the preselected sequence. The preselected sequence is preferably bound to a solid support as one member of a grid having a group of sequences.

11 Claims, 5 Drawing Sheets

EXAMPLE:
0a  GATCTT......
1b  CATGTT......
3j  GTTCTT......
4d  GATCGT......
2a  AATCCT......
•
•
•

1. EACH LOCATION OF THE ARRAY CONTAINS A UNIQUE PRESELECTED NUCLEIC ACID SEQUENCE.

2. THE GRID CAN BE ANY SIZE, SHAPE AND ORGANIZATION.

3. THE PRESELECTED NUCLEIC ACID SEQUENCE CAN BE FROM ANY SOURCE AND OF ANY LENGTH. PREFERABLY THE PRESELECTED NUCLEIC ACID SEQUENCE IS A SYNTHETIC OLIGONUCLEOTIDE 15-25 NUCLEOTIDES LONG.

METHOD OF DETECTING AND DISCRIMINATING BETWEEN NUCLEIC ACID SEQUENCES

This application is a 371 of PCT/US92/05133, filed Jun. 17, 1992.

This invention was made with government support under Grant No. HG00099 awarded by the National Institutes of Health. The government has certain rights in the invention.

FIELD OF INVENTION

The present invention relates to a method for detecting and for discriminating between nucleic acid sequences if present in a sample. More specifically, the invention relates to a method for determining if a particular DNA or RNA sequence is present in a sample. The invention also relates to discriminating between sequences which differ from each other by as little as a single nucleotide. The DNA or RNA may be single or double stranded, and may be a single species or a component of a mixture of nucleic acids. The method of the invention utilizes a novel primer design. The sequence of the primer is composed of two portions, the 3' portion is a primer specific for the target nucleic acid sequence and the 5' portion is complementary to a preselected nucleic acid sequence. Extension of the 3' portion of the primer with labeled deoxynucleosides triphosphate yields a labeled extension product if, but only if, the template includes the target sequence. The labeled extension product is detected by hybridization of the 5' portion to the preselected sequence.

BACKGROUND OF THE INVENTION

The genome of an organism is unique. Not only do the genomes of different species differ, but the genomes of different individuals within a species differ (with the exception of identical twins or clones). These differences provide individual and species specific characteristics which can be used for identification by nucleic acid biochemical techniques such as hybridization and polymerase mediated reactions, both dependent for their specificity on precise base pairing.

The goal of nucleic acid based diagnostics is the detection of specific nucleic acid sequences. This goal often requires the detection of a specific sequence in the presence of other sequences. In certain cases it is necessary to discriminate between closely related sequences, even sequences which differ by only a single nucleotide. Prior art methods for doing so are described in various publications. For example, the use of allele-specific oligonucleotide (ASO) hybridization probes for the detection of specific nucleic acid sequences has been described (Wu et al., *DNA* 8:135–142 (1989); Thein, et al., *Br. J. Haematol.* 70:225–231 (1988); Connor, et al., *Proc. Natl. Acad. Sci. USA* 80:278–282 (1983); Studencki, et al., *Am. J. Hum. Genet.* 37:42–51 (1985); Pirastu, et al., *N.Engl.J.Med.* 309:284–287 (1983); Orkin, et al., *J.Clin.Invest.* 71:775–779 (1983); Thein and Wallace, The use of synthetic oligonucleotides as specific hybridization probes in the diagnosis of genetic disorders. In Human genetic diseases: A practical approach. K. E. Davies, ed. (Oxford; IRL Press), pp. 33–50 (1986)). This approach allows the discrimination between nucleic acids which differ by as little as a single nucleotide (e.g., alleles). Individual hybridization reactions are required for each allele to be detected. Erlich, et al., *Eur.J.Immunogenet.* 18:33–55 (1991) and Zhang, et al., *Nucleic Acids Res.* 19:3929–3933 (1991) have recently described the use of immobilized ASO probes. In this method, a set of ASO probes is immobilized on a membrane and hybridized with labeled polymerase chain reaction (PCR) products. Under appropriate conditions hybridization is allele specific. Each hybridization can analyze only a single amplification reaction. The present invention allows for the detection of specific sequences in a sample. Because the template specific step and the detection step are each controlled by specific but independent base pairing requirements, the overall process allows detection of multiple templates and multiple samples simultaneously.

The concept of in vitro DNA amplification was first proposed by Khorana and coworkers in 1971 (Kleppe, et al., *J.Mol.Biol.* 56:341–361 (1971)). Realizing that total chemical synthesis of a gene would result in a finite amount of product, a procedure for in vitro replication was proposed. Their procedure was based on extensive studies of the repair replication reaction, the in vitro replication of a DNA template using a complementary primer (Kleppe, supra). Their proposal was as follows: "The DNA duplex would be denatured to form single strands. This denaturation step would be carried out in the presence of a sufficiently large excess of the two appropriate primers. Upon cooling, one would hope to obtain two structures, each containing the full length of the template strand appropriately complexed with the primer. DNA polymerase will be added to complete the process of repair replication. Two molecules of the original duplex should result. The whole cycle could be repeated, there being added every time a fresh dose of the enzyme." More recently, this in vitro amplification process has been further developed into the polymerase chain reaction (Mullis, et al., *Cold Spring Harbor Symp. Quant. Biol.* 51:263–273 (1986); Saiki, et al., *Science* 230:1350–1354 (1985); U.S. Pat. No. 4,683,202). Although template amplification improves detection of a particular sequence because a larger amount of template is available for analysis, post amplification steps are often required to detect specific sequences within the amplified product. For example, ASO hybridization has been combined with PCR amplification for the specific detection of various disease alleles (Impraim, et al., *Biochem. Biophys. Res. Commun.* 142:710–716 (1987); Saiki, et al., *Nature* 324:163–166 (1986); Farr, et al., *Proc.Natl. Acad.Sci. USA* 85:1629–1633 (1988); Saiki, et al., *N.Engl.J.Med.* 319:537–541 (1988); Chehab, et al., *Nature* 329:293–294 (1987)). The present invention provides an alternative for the analysis of PCR amplification products to determine the presence or absence of specific sequences.

SUMMARY OF THE INVENTION

This invention provides a method for determining the presence or absence of a target nucleic acid sequence present in a sample and for discriminating between any two nucleic acid sequences even if such sequences differ only by a single nucleotide. The nucleic sequences may be single or double stranded DNA or RNA. The target sequence may be relatively pure species or a component of a nucleic acid mixture. It may be produced by an in vitro amplification such as a PCR or ligation amplification reaction or by a plurality of cycles of primer extension.

The method of the invention entails extension of a novel two component primer on templates which may or may not include a target nucleic acid sequence. The 3' portion of the primer is complementary to a portion of the template adjacent the target sequence. The 5' portion of the primer is complementary to a different preselected nucleic acid sequence. Extension of the 3' portion of the primer with a labeled deoxynucleoside triphosphates yields a labeled extension product if, but only if, the template includes the target sequence. The presence of such a labeled primer extension product is detected by hybridization of the 5' portion to the preselected sequence. The preselected sequence is preferably immobilized on a solid support. A plurality of preselected sequences immobilized on a solid support to provide an array for concurrent screening of a plurality of labeled primer extension products is provided.

One practical embodiment of the invention relates to methods for diagnosing diseases such as sickle cell anemia or thalassemia caused by a defective allele. Kits for performing such a diagnosis are provided.

DEFINITIONS

As used herein, the following words have the meaning set forth:

"Oligonucleotide" refers to a nucleic acid sequence composed of two or more nucleotides. It can be derived from natural sources but is often synthesized chemically. It can be of any length. It is generally used as a primer, a probe or a component of ligation reaction.

"Primer" refers to an oligonucleotide which is used to initiate nucleic acid synthesis by a template dependent polymerase such as a DNA polymerase. The primer is complementary to a portion of a template nucleic acid.

"Primer extension" refers to the process of elongation of a primer on a nucleic acid template. Using appropriate buffers, pH, salts and nucleoside triphosphates, a template dependent polymerase such as a DNA polymerase incorporates a nucleotide complementary to the template strand on the 3' end of a primer which is annealed to a template. The polymerase will thus synthesize a faithful complementary copy of the template. If only a single nucleoside triphosphate is present in a primer extension reaction, then that nucleotide will be incorporated in the primer extension product only if the base of the nucleoside triphosphate is complementary to the base of the template immediately adjacent to the 3' end of the primer.

"Allele" refers to one of two or more alternative forms of a gene occupying corresponding sites (loci) on homologous chromosomes. The DNA sequence of alleles of a locus differ from each other by at least one nucleotide.

"Target" refers to the nucleic acid sequence to be detected or discriminated.

"Sample" refers to a nucleic acid which may or may not contain the target. The sample nucleic acid may be DNA or RNA, single or double stranded and present in a relatively pure form in the sample or one component of a mixture in the sample. In the case of RNA it is often useful to convert the RNA into DNA using a reverse transcription step. The DNA product can then be analyzed directly or subjected to an amplification step prior to analysis by the present invention.

"Allele specific primer extension (ASPE)" refers to a method as disclosed in copending application Ser. No. 07/683,137 filed Apr. 10, 1991 pursuant to which an oligonucleotide primer is annealed to a DNA template 3' with respect to a nucleotide indicative of the presence or absence of a target allelic variation. The primer is then extended in the presence of labelled dNTP in which the N is complementary to the nucleotide indicative of the presence or absence of the target allelic variation in the template.

DETAILED DESCRIPTION OF THE INVENTION

Figure 1:
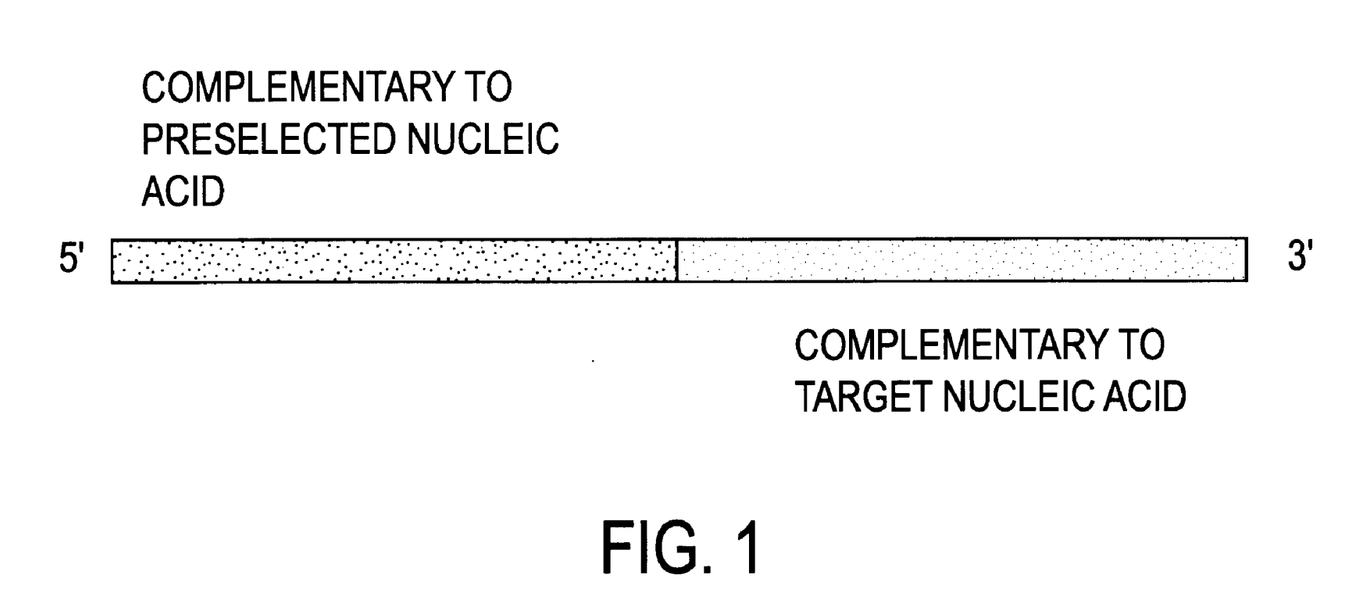
FIG. 1 depicts a two component primer useful in this invention.

The invention is described by reference to the Figures. As shown by FIG. 1, the 3' portion of the primer is complementary to a sequence adjacent a target sequence which may or may not be present in a sample. The 5' portion of the primer is complementary to a known or preselected sequence preferably immobilized on a solid support and arranged in a particular pattern. The two components of the primer may have any desired number of nucleotides. The number of nucleotides in each portion of the primer may be the same or different. Preferably each portion of the primer contains from about 10 to about 100 nucleotides. The word "about" indicates a variance e.g., of plus or minus ten nucleotides.

Figure 2:
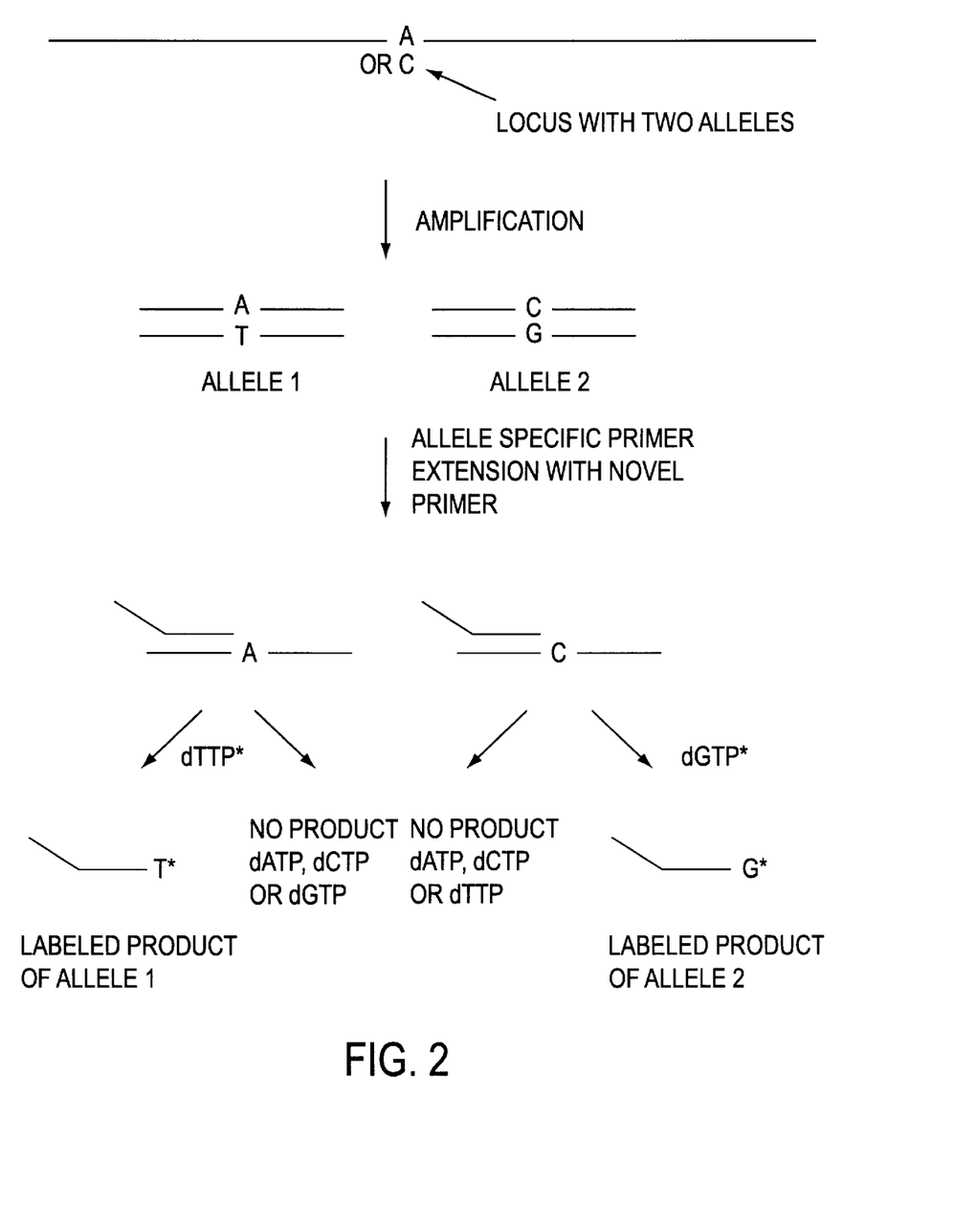
FIG. 2 depicts one embodiment of the invention.

FIG. 2 illustrates the principle of the invention as applied to identify and discriminate between two allelic nucleic acid sequences which may be present in a sample and which differ by a single nucleotide. As illustrated, a sample may contain either "A-T" or "C-G" alleles.

The primer is hybridized to the alleles immediately adjacent the variant nucleotides responsible for the allelism. ASPE reactions are performed with each of four labeled deoxynucleoside triphosphates independently. Only one of the primer extension reactions will label the primer for each of the different alleles.

As specifically depicted by FIG. 2, the amplification product is subjected to hybridization with a primer which includes a 3' portion complementary to the "A-T" allele which is then subjected to extension with labeled dNTP. Extension will occur only with dTTP if the A-T allele is present in the sample. No extension occurs with ATP, dCTP or dGTP.

Figure 3:
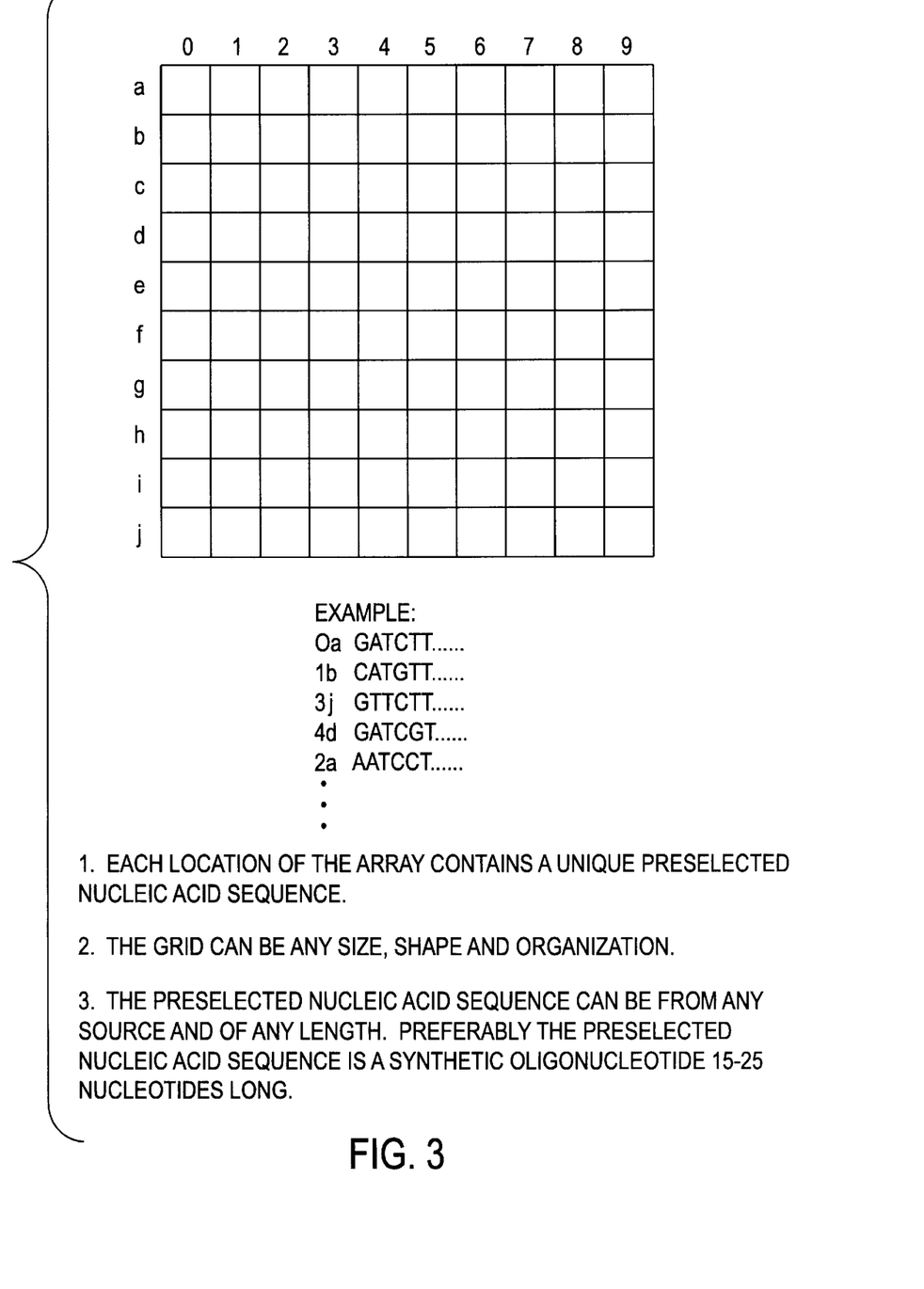
FIG. 3 depicts a solid support having a plurality of preselected sequences immobilized in a particular array on a grid.

The labeled primer extension product is screened by hybridization of the 5' portion of the labeled primer with the solid support depicted by FIG. 3. Each location on the array of sequences contains a different preselected oligonucleotide. The solid support may be of any size with any desired number of locations. The preselected oligonucleotides immobilized at each of the grid locations are preferably at least 10–100, preferably 15 to 25 nucleotides in length. Hybridization preferably, but not necessarily, occurs under substantially the same conditions at each location on the array.

The present invention is suitable for the detection of any nucleic acid. For example, if a sample were suspected of containing a nucleic acid specific for a pathogen, the sample could be analyzed by the present invention. A novel primer would be synthesized with a 3' portion specific for the pathogen genome and a 5' portion complementary to a preselected sequence. The sample would be either analyzed directly or after amplification by PCR.

The present invention is also suitable for discriminating between individuals on the basis of genetic differences. For example, the determination of which alleles are prosert at 20 different dimorphic, genetically unlinked loci would provide a powerful method useful in forensic science to discriminate between different individuals. The present invention is useful, e.g., in transplantation medicines, to determine which HLA alleles are present in a DNA sample of an individual.

EXEMPLIFICATION OF THE INVENTION

EXAMPLE I

Experimental Design

The first step, not shown, involves the amplification of the target sequence with a primer set (TYR 1 and TYR 2) specific for the TYR locus. After the amplification, the template is prepared for the next step by eliminating the remaining dNTPs.

EXAMPLE II

Synthesis of Oligonucleotides

Chemical Synthesis of Oligonucleotide Primers

Oligonucleotides were synthesized on a Cruachem PS 250 DNA synthesizer. Oligonucleotides for amplifying the target sequence (TYR 1 and TYR 2) were purified by HPLC. The oligonucleotide used in the allele specific primer extension reactions (ASPE primer) was purified by HPLC followed by a 20% polyacrylamide gel/7M urea. The sequences of the synthetic oligonucleotides utilized are presented in Table 1.

TABLE 1

| | Oligonucleotide Sequences Specific For TYR | |
|---|---|---|
| TYR 1 | 5'GCAAGTTTGGCTTTTGGGGA | SEQ ID NO:1 |
| TYR 2 | 5'CTGCCAAGAGGAGAAGAATG | SEQ ID NO:2 |
| ASPE primer | 5'TGACGTCCATCGTCTCTGCGAATGTCTCTCCAGATTTCA | SEQ ID NO:3 |

Figure 4:
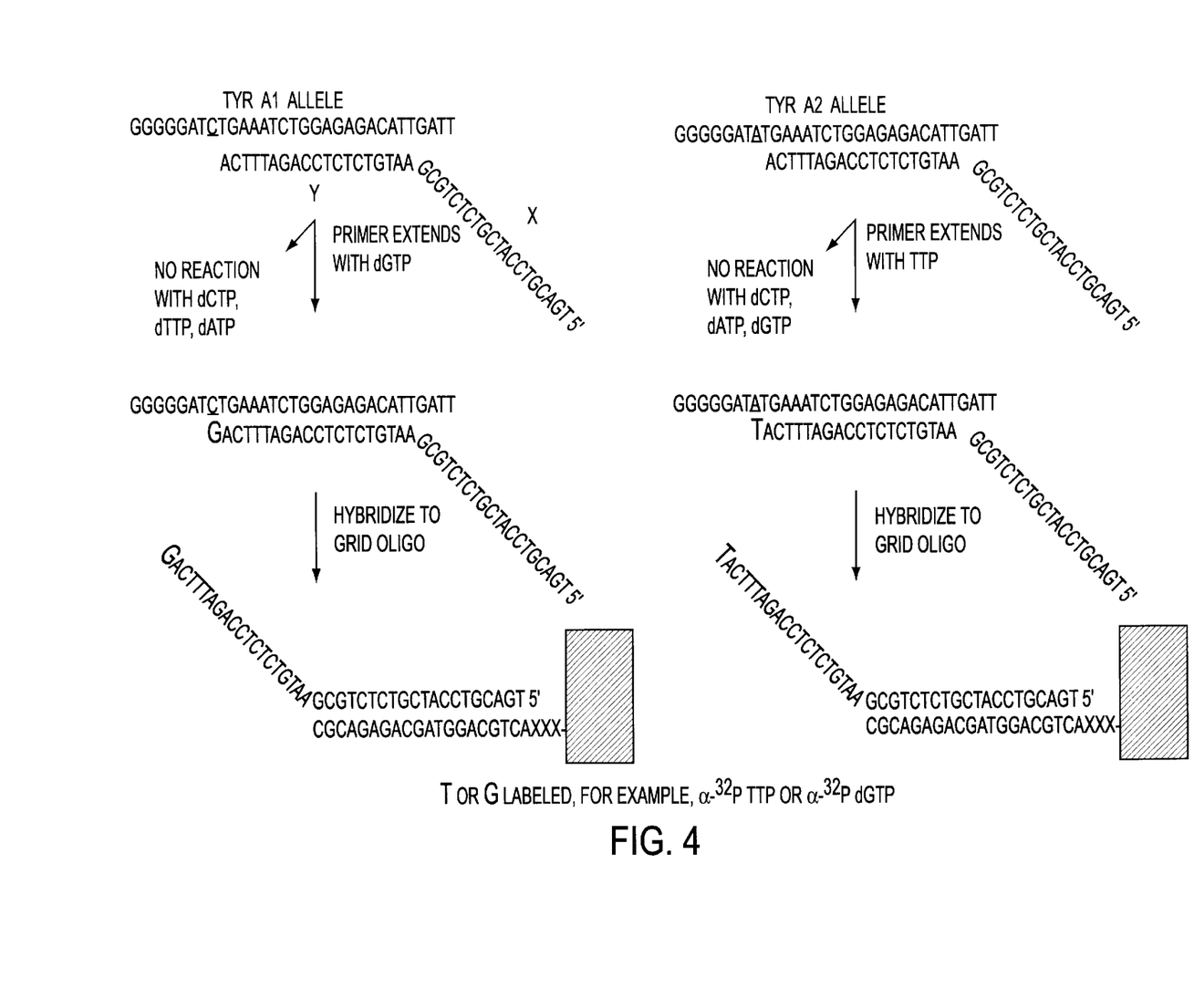
FIG. 4 depicts the application of the present invention for the detection of alleles of the human TYR locus.

FIG. 4 shows an overview of the procedure called ASPE-capture, applied in this example to the detection of the amplified dimorphic sequence present at the TYR locus produced by the first step.

The method consists of three steps. This procedure is locus and allele specific in that it is designed both to specifically detect the presence of the amplification product and to determine the target identifying polymorphic nucleotide of the analyzed locus. FIG. 4 depicts two separate primer extension reactions which have as common ingredients the DNA template, the ASPE primer, and the Ampli-Taq polymerase. The two reactions differ in that they contain different nucleoside triphosphates: allele A1 is detected by including $\alpha$-$^{32}$P dGTP and allele A2 by including $\alpha$-$^{32}$P TTP. The ASPE primer is a 40 nucleotide long oligonucleotide which includes two different portions (X and Y) each having a different role. Sequence Y is identical to the sense sequence of the TYR gene with its 3' nucleotide immediately flanking the polymorphic base. This portion of the ASPE primer participates in the primer extension reaction. Y sequence is extended by the Ampli-Taq DNA polymerase whenever an $\alpha$-$^{32}$P labeled nucleotide complementary to the polymorphic base is present in the reaction. For a DNA template from individuals homozygous for the TYR-A1 allele, the ASPE primer will be only extended by $\alpha$-$^{32}$P labeled dGTP. $\alpha$-$^{32}$P labeled TTP will be added to the ASPE primer when a DNA template from individuals homozygous for the TYR-A2 allele is analyzed. Both labeled nucleoside triphosphates will be added to the ASPE primer for DNA templates from heterozygous individuals. It should be noted that if no template is present, no labeling of the ASPE primer will happen. Sequence X is complementary to a grid oligonucleotide, thus permitting capture of the primer extension product on the grid.

This invention is not limited to the described steps. For example, the labeling of the primer extension product could be accomplished using fluorescently labeled deoxynucleoside triphosphates or dideoxynucleoside triphosphates. The capture could be accomplished by hybridization in solution to an oligonucleotide which can later be immobilized (for example by utilizing biotin-avidin, hapten-antibody reactions).

Chemical Synthesis of Grid Oligonucleotide

The grid oligonucleotide for attachment to the nylon membrane was prepared as follows: 3'Amine-ON CPC columns (0.2 $\mu$mole) were purchased from Cruachem and were used on the Cruachem PS 250 DNA synthesizer. Three 1,3 propanediol nucleoside substitutes were coupled directly to the column prior to coupling the grid oligonucleotide sequence. The protected 1,3 propanediol phosphoramidite was prepared essentially as described by Seela and Kaiser, *Nucleic Acids Res.* 15:3113–3129 (1987). This phosphoramidite was placed in the X position of the synthesizer. For example to synthesize the grid oligonucleotide for the detection of TYR extension products, the synthesizer was programmed to synthesize 5'CGCAGAGACGATGGACGT-CAXXX SEQ. ID. No 26. The oligonucleotide is deprotected as usual and the oligonucleotide recovered by ethanol precipitation. The oligonucleotide contains a 3'NH$_2$ group.

Preparation of the Filters Containing Grid Oligonucleotides

The membranes containing the grid oligonucleotides were prepared according to Zhang, et al., *Nucleic Acids Res.* 19:3929–3933 (1991). Briefly, Biodyne C membranes (Pall Biosupport, N.J.) were rinsed with 0.1N HCl and then treated for 15 minutes with 20% EDC (1-Ethyl-3-[dimethylamion propyl] carbodiimide hydrochloride) (w/v) in deionized water. After the activation process, the membranes were immediately set in a 96 well Bio-dot apparatus (Bio-Rad, Richmond, Calif.). The grid oligonucleotide was mixed with 0.5 M sodium bicarbonate buffer pH 8.4 and applied to the membranes for 15 minutes. The membranes were rinsed with TBS/0.1% Tween-20 (Tris buffered saline) and then treated with 0.1 N NaOH for 10 minutes. Finally, filters were rinsed with deionized water.

EXAMPLE III

Allele Specific Detection Reactions
Isolation of Genomic DNA

Blood samples were collected from ten unrelated individuals. High molecular weight DNA was prepared according to a modified procedure using Triton X-100 followed by Proteinase K and RNAse treatment (Bell, et al., *Proc. Natl. Acad. Sci. USA* 78:5759–5763 (1981)).

In Vitro Amplification of DNA Template

DNA (50 ng) from ten random individuals was amplified with a primer set derived from exon I of the human tyrosinase gene (TYR) (GenBank Accession M27160; Locus HUMTYRA) in a 50 µl reaction volume containing 50 mM KCl, 10 mM Tris-HCl (pH 8.3), 1.5 mM MgCl$_2$, 0.01% (w/v) gelatin, 10 pmol of each primer, 0.2 mM each dATP, dCTP, dGTP, TTP, and 2.5 units of Ampli-taq polymerase (Perkin Elmer Cetus). The reaction was performed in a thermal cycler (Perkin Elmer). The reaction mixture was denatured at 94° C. for 3 minutes, then the cycle was continued by annealing the primers at 65° C. for 1 minute and extending the primers at 72° C. for 1 minute. After extension, the samples were denatured at 94° C. for 30 seconds. The annealing, extension, and denaturation cycle was repeated 40 times. After the last cycle, the samples were incubated at 65° C. for 1 minute, at 72° C. for 6 minutes and finally at 4° C. until analyzed.

Preparation of DNA Template for Primer Extension Reactions

In order to control the quality of the PCR products, 5 µl were loaded in a 1.5% agarose gel. The remaining 45 µl were ethanol precipitated twice using 2.5 M ammonium acetate and 10 µg of glycogen. The pellet was resuspended in H$_2$O (100 µl).

Allele-specific Primer Extension Reactions

Each allele-specific primer extension reaction (ASPE) was performed in a 10 µl volume containing 1 µl of PCR template, 1 µl of 10× PCR buffer (1×=10mM Tris-HCl pH 8.3, 50 mM KCl, 1.5 mM MgCl2), 0.01% (w/v) gelatin, 0.25 µM of ASPE primer, 1 unit of Ampli-taq polymerase, and 0.5 µl of the appropriate α-$^{32}$P-labeled nucleotide (10 µCi/µl, 3000 Ci/mmol). To analyze the dimorphism present at locus TYR, each sample was subjected to two separate primer extension reactions using µ-$^{32}$P labeled dGTP and TTP respectively. Mixtures were denatured at 94° C. for 3 minutes and then subjected to 10 cycles consisting of 1 second annealing at 55° C. and 30 seconds denaturation at 94° C. After the reaction, samples were ethanol precipitated and used for hybridization.

Hybridization and Post Hybridization Washes

All the hybridizations were performed overnight at 55° C. in 2 ml microcentrifuge tubes using hybridization incubator (Robbins Scientific, model 310). The hybridizations were done in a 225 µl volume (Hybridization solution: 5×SSPE [1×SSPE=10 mM sodium phosphate pH 7.0, 0.18 M NaCl and 1 mM EDTA], 1% SDS, 0.5% (w/v) dehydrated powdered skim milk (Carnation, Los Angeles, Calif.), 10 µg/ml homomix RNA, and the product of the primer extension reaction). After hybridization, the filters were washed with 6×SSC (1×SSC=0.15 M NaCl, 0.015 M sodium citrate) at room temperature for 15 minutes. Autoradiography of membranes was done using Kodak X-AR5 film and exposing for 15–30 minutes at room temperature. Subsequently, the amount of cpm corresponding to the labelled ASPE bound to the filter was measured by Ambis-scan (Ambis Corp., San Diego, Calif.).

Figure 5:
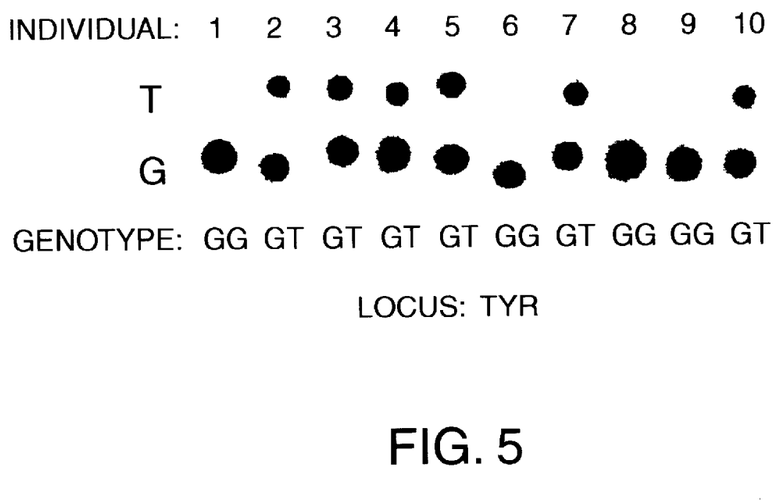
FIG. 5 depicts the genotypic analysis of ten individuals for alleles at the TYR locus using the invention.

The results of hybridization are shown in FIG. 5. Note that of the ten individuals analyzed, six are heterozygous (2, 3, 4, 5, 7 and 10) and four are homozygous for the TYR-A1 allele.

EXAMPLE IV

Grid Oligonucleotides

General Approach for the Design of Grid Design of Grid Oligonucleotide Sequences Grid oligonucleotides were designed to be 20 nucleotides in length and to have a base composition of 50% G+C. This design allows hybridization reactions to be carried out with a single hybridization temperature for all sequences. The first 20 grid oligonucleotide sequences were generated by starting with the sequence 5'GGGGGCCCCCTTTT-TAAAAA (25% of each of the four bases). This sequence was then randomized by the RANDOMIZATION option (group length 1, randomize all) within the program GENED in the Intellegenetic Suite software for molecular biology (Intelligenetics, Mountain View, Calif.) to give the first sequence in Table 2. Each of the next 19 sequences were generated by randomizing the previous sequence in the list.

TABLE 2

| Examples of grid oligonucleotide sequences | |
|---|---|
| 5'TCGCGTTGCATAAGATCCGA | SEQ ID NO:4 |
| 5'CTTAACGAAAGCTGCGGTCT | SEQ ID NO:5 |
| 5'TTCGAGCTCCAGTTAACGAG | SEQ ID NO:6 |
| 5'TCTCTATGTCGGAAGAGCCA | SEQ ID NO:7 |
| 5'CATAATGCGGTCTCGATACG | SEQ ID NO:8 |
| 5'ATTGCCGTCCGTAGGACTAA | SEQ ID NO:9 |
| 5'TCTATCACGGACTATCGGGA | SEQ ID NO:10 |
| 5'TTGTCACAGGCACAATGTGC | SEQ ID NO:11 |
| 5'CGAAGAGCCATGATGCTTCT | SEQ ID NO:12 |
| 5'AGACGTCGTCACGATTCTGA | SEQ ID NO:13 |
| 5'ACACGTGCGCCTGGAATTAT | SEQ ID NO:14 |
| 5'CAGGTGCCATATAATGGTCC | SEQ ID NO:15 |
| 5'TGGCCATACCAGACTTTAGG | SEQ ID NO:16 |
| 5'ATGGGCTCCTGCGTAAATCA | SEQ ID NO:17 |
| 5'AGTGCGCTCTCTTGAGCAAA | SEQ ID NO:18 |
| 5'ACTGTTACCGGTAACTGACG | SEQ ID NO:19 |
| 5'GATATACCATTCCAGGCGTG | SEQ ID NO:20 |
| 5'TCCGGCTCATGGTAGAATAC | SEQ ID NO:21 |
| 5'CTTACAATATCCGGCGTGGA | SEQ ID NO:22 |
| 5'GGGTATTCTCGACCAATCAG | SEQ ID NO:23 |

Similarly, additional grid oligonucleotides can be generated starting with other sequences which are 50% G-C (e.g., 5'AAATTTTTTTGGGCCCCCCC, SEQ. ID. No. 24. 5'GGGGGGGCCCAAAAAATTTT) SEQ. ID. No. 25.

EXAMPLE V

Removal of Deoxynucleoside Triphosphates

An important step in the practice of this invention is the removal of the deoxynucleoside triphosphates (dNTPs), if present, from the sample to be subjected to the primer extension reaction. This can be accomplished by several methods including ethanol precipitation of the template DNA (as described in Example III), by destruction of the dNTPs with an enzyme or by chromatography on a column which can separate polymerized nucleic acids from dNTPs.

In the latter approach, a column of DE52 was prepared. DE52 (Whatman) was suspended in a buffer containing 10 mM Tris-HCl, pH 7.5 (TE) such that the ratio of DE52 to buffer was 1:2. The DE52 suspension (0.2 ml) was poured into a 1 ml micropipette tip (e.g., the blue tip for Gilson P-1000 Pipetman™) which had been plugged with glass wool and washed with 1 ml of TE. The sample (e.g., the product of a polymerase chain reaction) was diluted to 0.1 ml with TE and applied to the column under slight air pressure. The column was washed with 1 ml of TE. The dNTPs were eluted with 4×0.5 ml of 0.2 M NaCl. Finally, the sample was recovered, essentially free of dNTPs by 0.2 ml 1M NaCl. The sample could then be used directly in a primer extension reaction.

I claim:

1. An allele specific primer having a 3' portion and a 5' portion
   wherein said 3' portion is complementary to a target sequence adjacent an allele specific nucleotide, and
   wherein said 5' portion is complementary to a preselected and randomly generated nucleic acid sequence which is different from said target sequence and which said preselected nucleic acid sequence is immobilized at a preselected location in an array of immobilized, preselected and randomly generated nucleic acid sequences on a solid support, wherein the length, base composition and percentage of each base in each of said immobilized preselected nucleic acid sequences are substantially the same to permit hybridization between said 5' portion and said preselected nucleic acid sequence to be carried out at the same temperature for all said immobilized preselected nucleic acid sequences.

2. The allele specific primer of claim 1, wherein the location of the immobilized preselected nucleic acid sequence is associated with a locus of the target sequence.

3. The allele specific primer of claim 1, wherein the preselected nucleic acid sequence is an oligonucleotide immobilized at a preselected location in an array of immobilized oligonucleotides on a solid support.

4. A method for identifying an allele specific nucleotide in a target nucleic acid sequence in a nucleic acid sample, said method comprising (a) combining under hybridizing conditions to form a duplex
   (i) a nucleic acid sample which may include a target nucleic acid sequence,
   (ii) an allele specific primer having a 3' portion and a 5' portion
   wherein said 3' portion is complementary to a target nucleic acid sequence adjacent an allele specific nucleotide, and
   wherein said 5' portion is complementary to a preselected and randomly generated nucleic acid sequence which is different from said target nucleic acid sequence and which said preselected nucleic acid sequence is immobilized at a preselected location in an array of immobilized, preselected and randomly generated nucleic acid sequences on a solid support, wherein the lengths base composition and percentage of each base in each of said immobilized preselected nucleic acid sequences are substantially the same to permit hybridization between said 5' portion and said preselected nucleic acid sequence to be carried out at the same temperature for all said immobilized preselected nucleic acid sequences, (b) adding a DNA polymerase and deoxynucleoside triphosphates, one of which is an allele specific nucleotide containing a label, to the duplex of step (a), if present, under conditions to form an allele specific labeled primer extension product which includes the 3' and 5' portions of the allele specific primer of (a)(ii), (c) screening the allele specific labeled primer extension product of (b) by combining the 5' portion with the array of immobilized, preselected and randomly generated nucleic acid sequences on the solid support whereby the label identifies the allele specific nucleotide and the location of the immobilized preselected nucleic acid sequence is associated with the locus of the target nucleic acid sequence in the nucleic acid sample.

5. The method of claim 4, wherein the preselected nucleic acid sequence is an oligonucleotide immobilized at a preselected location in an array of immobilized oligonucleotides on a solid support.

6. The method of claim 4, wherein said nucleic acid sample may contain a plurality of target nucleic acid sequences and wherein said nucleic acid sample is subjected to polymerase chain reaction amplification with at least one pair of oligonucleotide primers for two or more of said target nucleic acid sequences.

7. The method of claim 6, wherein said target nucleic acid sequences are alleles of one another, the 3' portion of said primer is positioned immediately adjacent to the variant nucleotide responsible for the allelism, and said primer extension reactions are independently performed with each of the four deoxynucleoside triphosphates such that only one primer extension reaction will occur for each of said alleles, said deoxynucleoside triphosphate being labeled whereby a single labeled primer extension product is produced for each of said alleles.

8. A solid support for capturing a plurality of nucleic acids, each of said nucleic acids having a 3' portion complementary to a target sequence and a 5' portion, said solid support comprising a plurality of immobilized, preselected and randomly generated nucleic acid sequences, wherein the length, base composition and percentage of each base in each of said immobilized preselected nucleic acid sequences are substantially the same to permit hybridization between said 5' portion and its complementary preselected nucleic acid sequence to be carried out at the same temperature for all said immobilized preselected nucleic acid sequences.

9. The solid support of claim 8, wherein the location of the immobilized preselected nucleic acid sequences is associated with a locus of the target sequence.

10. The solid support of claim 8, wherein each of the preselected nucleic acid sequences is an oligonucleotide immobilized at a preselected location in an array of immobilized oligonucleotides.

11. The solid support of claim 8, wherein the length, base composition, and percentage of each base in each of said immobilized preselected nucleic acid sequences are identical.

* * * * *

```
                         SEQUENCE LISTING (1) GENERAL INFORMATION:

(iii) NUMBER OF SEQUENCES:  27

(2) INFORMATION FOR SEQ ID NO:1:

(i) SEQUENCE CHARACTERISTICS:
           (A) LENGTH:  20
           (B) TYPE:  Nucleotide
           (C) STRANDEDNESS:  Single
           (D) TOPOLOGY:  Linear (xi) SEQUENCE DESCRIPTION: SEQ ID NO: 1:

GCAAGTTTGG CTTTTGGGGA                                                  20

(2) INFORMATION FOR SEQ ID NO:2:

(i) SEQUENCE CHARACTERISTICS:
           (A) LENGTH:  20
           (B) TYPE:  Nucleotide
           (C) STRANDEDNESS:  Single
           (D) TOPOLOGY:  Linear (xi) SEQUENCE DESCRIPTION: SEQ ID NO: 2:

CTGCCAAGAG GAGAAGAATG                                                  20

(2) INFORMATION FOR SEQ ID NO:3:

(i) SEQUENCE CHARACTERISTICS:
           (A) LENGTH:  39
           (B) TYPE:  Nucleotide
           (C) STRANDEDNESS:  Single
           (D) TOPOLOGY:  Linear (xi) SEQUENCE DESCRIPTION: SEQ ID NO: 3:

TGACGTCCAT CGTCTCTGCG AATGTCTCTC CAGATTTCA                             39

(2) INFORMATION FOR SEQ ID NO:4:

(i) SEQUENCE CHARACTERISTICS:
           (A) LENGTH:  20
           (B) TYPE:  Nucleotide
           (C) STRANDEDNESS:  Single
           (D) TOPOLOGY:  Linear (xi) SEQUENCE DESCRIPTION: SEQ ID NO: 4:

TCGCGTTGCA TAAGATCCGA                                                  20

(2) INFORMATION FOR SEQ ID NO:5:

(i) SEQUENCE CHARACTERISTICS:
           (A) LENGTH:  20
           (B) TYPE:  Nucleotide
           (C) STRANDEDNESS:  Single
           (D) TOPOLOGY:  Linear (xi) SEQUENCE DESCRIPTION: SEQ ID NO: 5:

CTTAACGAAA GCTGCGGTCT                                                  20
```

(2) INFORMATION FOR SEQ ID NO:6:

(i) SEQUENCE CHARACTERISTICS:
        (A) LENGTH: 20
        (B) TYPE: Nucleotide
        (C) STRANDEDNESS: Single
        (D) TOPOLOGY: Linear     (xi) SEQUENCE DESCRIPTION: SEQ ID NO: 6:

TTCGAGCTCC AGTTAACGAG                                      20

(2) INFORMATION FOR SEQ ID NO:7:

(i) SEQUENCE CHARACTERISTICS:
        (A) LENGTH: 20
        (B) TYPE: Nucleotide
        (C) STRANDEDNESS: Single
        (D) TOPOLOGY: Linear     (xi) SEQUENCE DESCRIPTION: SEQ ID NO: 7:

TCTCTATGTC GGAAGAGCCA                                      20

(2) INFORMATION FOR SEQ ID NO:8:

(i) SEQUENCE CHARACTERISTICS:
        (A) LENGTH: 20
        (B) TYPE: Nucleotide
        (C) STRANDEDNESS: Single
        (D) TOPOLOGY: Linear     (xi) SEQUENCE DESCRIPTION: SEQ ID NO: 8:

CATAATGCGG TCTCGATACG                                      20

(2) INFORMATION FOR SEQ ID NO:9:

(i) SEQUENCE CHARACTERISTICS:
        (A) LENGTH: 20
        (B) TYPE: Nucleotide
        (C) STRANDEDNESS: Single
        (D) TOPOLOGY: Linear     (xi) SEQUENCE DESCRIPTION: SEQ ID NO: 9:

ATTGCCGTCC GTAGGACTAA                                      20

(2) INFORMATION FOR SEQ ID NO:10:

(i) SEQUENCE CHARACTERISTICS:
        (A) LENGTH: 20
        (B) TYPE: Nucleotide
        (C) STRANDEDNESS: Single
        (D) TOPOLOGY: Linear     (xi) SEQUENCE DESCRIPTION: SEQ ID NO: 10:

TCTATCACGG ACTATCGGGA                                      20

(2) INFORMATION FOR SEQ ID NO:11:

(i) SEQUENCE CHARACTERISTICS:
        (A) LENGTH: 20
        (B) TYPE: Nucleotide
        (C) STRANDEDNESS: Single
        (D) TOPOLOGY: Linear     (xi) SEQUENCE DESCRIPTION: SEQ ID NO: 11:

TTGTCACAGG CACAATGTGC                                      20

(2) INFORMATION FOR SEQ ID NO:12:

```
        (i) SEQUENCE CHARACTERISTICS:
            (A) LENGTH: 20
            (B) TYPE: Nucleotide
            (C) STRANDEDNESS: Single
            (D) TOPOLOGY: Linear (xi) SEQUENCE DESCRIPTION: SEQ ID NO: 12:

CGAAGAGCCA TGATGCTTCT                                                    20

(2) INFORMATION FOR SEQ ID NO:13:

(i) SEQUENCE CHARACTERISTICS:
            (A) LENGTH: 20
            (B) TYPE: Nucleotide
            (C) STRANDEDNESS: Single
            (D) TOPOLOGY: Linear (xi) SEQUENCE DESCRIPTION: SEQ ID NO: 13:

AGACGTCGTC ACGATTCTGA                                                    20

(2) INFORMATION FOR SEQ ID NO:14:

(i) SEQUENCE CHARACTERISTICS:
            (A) LENGTH: 20
            (B) TYPE: Nucleotide
            (C) STRANDEDNESS: Single
            (D) TOPOLOGY: Linear (xi) SEQUENCE DESCRIPTION: SEQ ID NO: 14:

ACACGTGCGC CTGGAATTAT                                                    20

(2) INFORMATION FOR SEQ ID NO:15:

(i) SEQUENCE CHARACTERISTICS:
            (A) LENGTH: 20
            (B) TYPE: Nucleotide
            (C) STRANDEDNESS: Single
            (D) TOPOLOGY: Linear (xi) SEQUENCE DESCRIPTION: SEQ ID NO: 15:

CAGGTGCCAT ATAATGGTCC                                                    20

(2) INFORMATION FOR SEQ ID NO:16:

(i) SEQUENCE CHARACTERISTICS:
            (A) LENGTH: 20
            (B) TYPE: Nucleotide
            (C) STRANDEDNESS: Single
            (D) TOPOLOGY: Linear (xi) SEQUENCE DESCRIPTION: SEQ ID NO: 16:

TGGCCATACC AGACTTTAGG                                                    20

(2) INFORMATION FOR SEQ ID NO:17:

(i) SEQUENCE CHARACTERISTICS:
            (A) LENGTH: 20
            (B) TYPE: Nucleotide
            (C) STRANDEDNESS: Single
            (D) TOPOLOGY: Linear (xi) SEQUENCE DESCRIPTION: SEQ ID NO: 17:

ATGGGCTCCT GCGTAAATCA                                                    20

(2) INFORMATION FOR SEQ ID NO:18:

(i) SEQUENCE CHARACTERISTICS:
```

```
            (A) LENGTH:  20
            (B) TYPE:  Nucleotide
            (C) STRANDEDNESS:  Single
            (D) TOPOLOGY:  Linear (xi) SEQUENCE DESCRIPTION: SEQ ID NO: 18:

AGTGCGCTCT CTTGAGCAAA                                             20

(2) INFORMATION FOR SEQ ID NO:19:

(i) SEQUENCE CHARACTERISTICS:
            (A) LENGTH:  20
            (B) TYPE:  Nucleotide
            (C) STRANDEDNESS:  Single
            (D) TOPOLOGY:  Linear (xi) SEQUENCE DESCRIPTION: SEQ ID NO: 19:

ACTGTTACCG GTAACTGACG                                             20

(2) INFORMATION FOR SEQ ID NO:20:

(i) SEQUENCE CHARACTERISTICS:
            (A) LENGTH:  20
            (B) TYPE:  Nucleotide
            (C) STRANDEDNESS:  Single
            (D) TOPOLOGY:  Linear (xi) SEQUENCE DESCRIPTION: SEQ ID NO: 20:

GATATACCAT TCCAGGCGTG                                             20

(2) INFORMATION FOR SEQ ID NO:21:

(i) SEQUENCE CHARACTERISTICS:
            (A) LENGTH:  20
            (B) TYPE:  Nucleotide
            (C) STRANDEDNESS:  Single
            (D) TOPOLOGY:  Linear (xi) SEQUENCE DESCRIPTION: SEQ ID NO: 21:

TCCGGCTCAT GGTAGAATAC                                             20

(2) INFORMATION FOR SEQ ID NO:22:

(i) SEQUENCE CHARACTERISTICS:
            (A) LENGTH:  20
            (B) TYPE:  Nucleotide
            (C) STRANDEDNESS:  Single
            (D) TOPOLOGY:  Linear (xi) SEQUENCE DESCRIPTION: SEQ ID NO: 22:

CTTACAATAT CCGGCGTGGA                                             20

(2) INFORMATION FOR SEQ ID NO:23:

(i) SEQUENCE CHARACTERISTICS:
            (A) LENGTH:  20
            (B) TYPE:  Nucleotide
            (C) STRANDEDNESS:  Single
            (D) TOPOLOGY:  Linear (xi) SEQUENCE DESCRIPTION: SEQ ID NO: 23:

GGGTATTCTC GACCAATCAG                                             20

(2) INFORMATION FOR SEQ ID NO:24:

(i) SEQUENCE CHARACTERISTICS:
            (A) LENGTH:  20
            (B) TYPE:  Nucleotide
```

-continued

```
            (C) STRANDEDNESS:  Single
            (D) TOPOLOGY:  Linear (xi) SEQUENCE DESCRIPTION: SEQ ID NO: 24:

AAATTTTTTT GGGCCCCCCC                                                        20

(2) INFORMATION FOR SEQ ID NO:25:

(i) SEQUENCE CHARACTERISTICS:
            (A) LENGTH:  20
            (B) TYPE:  Nucleotide
            (C) STRANDEDNESS:  Single
            (D) TOPOLOGY:  Linear (xi) SEQUENCE DESCRIPTION: SEQ ID NO: 25:

GGGGGGGCCC AAAAAATTTT                                                        20

(2) INFORMATION FOR SEQ ID NO:26:

(i) SEQUENCE CHARACTERISTICS:
            (A) LENGTH:  23
            (B) TYPE:  Nucleotide
            (C) STRANDEDNESS:  Single
            (D) TOPOLOGY:  Linear (xi) SEQUENCE DESCRIPTION: SEQ ID NO: 26:

CGCAGAGACG ATGGACGTCA NNN                                                    23

(2) INFORMATION FOR SEQ ID NO:27:

(i) SEQUENCE CHARACTERISTICS:
            (A) LENGTH:  20
            (B) TYPE:  Nucleotide
            (C) STRANDEDNESS:  Single
            (D) TOPOLOGY:  Linear (xi) SEQUENCE DESCRIPTION: SEQ ID NO: 27:

GGGGGCCCCC TTTTTAAAAA                                                        20
```